US011045473B2

(12) United States Patent
Smiraglia et al.

(10) Patent No.: US 11,045,473 B2
(45) Date of Patent: Jun. 29, 2021

(54) COMPOSITIONS AND METHODS FOR THERAPY OF PROSTATE CANCER USING DRUG COMBINATIONS TO TARGET POLYAMINE BIOSYNTHESIS AND RELATED PATHWAYS

(71) Applicants: Health Research, Inc., Buffalo, NY (US); The Johns Hopkins University, Baltimore, MD (US)

(72) Inventors: Dominic Smiraglia, Buffalo, NY (US); Haley Affronti, Esopus, NY (US); Robert Casero, White Hall, MD (US)

(73) Assignees: Health Research, Inc., Buffalo, NY (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/575,043

(22) PCT Filed: May 17, 2016

(86) PCT No.: PCT/US2016/032838
§ 371 (c)(1),
(2) Date: Nov. 17, 2017

(87) PCT Pub. No.: WO2016/187183
PCT Pub. Date: Nov. 24, 2016

(65) Prior Publication Data
US 2018/0147207 A1 May 31, 2018

Related U.S. Application Data

(60) Provisional application No. 62/163,353, filed on May 18, 2015.

(51) Int. Cl.
| | | |
|---|---|---|
| *A61K 31/519* | (2006.01) | |
| *A61K 31/131* | (2006.01) | |
| *A61P 35/00* | (2006.01) | |
| *A61K 45/06* | (2006.01) | |
| *A61K 31/132* | (2006.01) | |

(52) U.S. Cl.
CPC .......... *A61K 31/519* (2013.01); *A61K 31/131* (2013.01); *A61K 31/132* (2013.01); *A61K 45/06* (2013.01); *A61P 35/00* (2018.01)

(58) Field of Classification Search
CPC .. A61K 31/519; A61K 31/131; A61K 31/132; A61K 45/06; A61P 35/00
See application file for complete search history.

(56) References Cited

U.S. PATENT DOCUMENTS

| 8,916,571 B2 | 12/2014 | Schramm et al. |
| 2002/0127714 A1 | 9/2002 | Housman et al. |
| 2008/0118437 A1 | 5/2008 | Pienta et al. |
| 2013/0045204 A1 | 2/2013 | Andersen et al. |

OTHER PUBLICATIONS

Porter et al. (Cancer Research 53. 581-586. Feb. 1, 1993) (Year: 1993).*
Dredge et al. (Cancer Chemother Pharmacol (2009) 65:191-195 (Year: 2009).*
Basu et al. (The Journal of Biological Chemistry vol. 286, No. 6, pp. 4902-4911, Feb. 11, 2011) (Year: 2011).*
Bistulfi et al. ("Methylthioadenosine phosphorylase is required for prostate cancer growth in vitro and in vivo (766.2)," Biochemistry and Molecular Biology The FASEB Journal vol. 28, No. 1_supplement Published Online, Apr. 1, 2014) (Year: 2014).*
Torres, I.M., Targeting the methionine salvage pathway as a metabolic point of leverage in novel therapeutic approaches for prostate cancer, SUNY Undergraduate Research Conference, Apr. 10, 2015, 2 pages. http://digitalcommons.brockport.edu/surc/2015/schedule/72/.
Schipper, R.G., et al., Antitumor Activity of the Polyamine Analog N[1],N[11]-Diethylnorspermine Against Human Prostate Carcinoma Cells, The Prostate, 2000, vol. 44, pp. 313-321.
Clower, C., et al., Androgen induced polyamine catabolic enzyme expression is a major cause of oxidative stress in prostate cancer cells, Proc. Amer. Assoc. Cancer Res., 2005, vol. 26, 2 pages.

* cited by examiner

*Primary Examiner* — Kortney L. Klinkel
*Assistant Examiner* — William Y Lee
(74) *Attorney, Agent, or Firm* — Hodgson Russ LLP

(57) ABSTRACT

Provided are compositions and methods for treating prostate conditions. The methods involve administering to an individual in need thereof a composition that contains i) an inhibitor of methionine salvage pathway in prostate of the individual and ii) a polyamine analogue. The methods are for use in individuals who have been diagnosed with, or are suspected of having or at risk for developing androgen sensitive prostate cancer (AS-CaP), or Castration recurrent CaP (CR-CaP), or benign prostate hyperplasia (BPH). The disclosure includes use of inhibitors of methylthioadenosine phosphorylase (MTAP), and a polyamine analog that upregulates polyamine catabolism by increasing spermidine/spermine N1-acetyl transferase (SAT1) activity, such as methyl-thio-DADMe-Immucillin (MTDIA), and 1),N(11)-bisethylnorspermine (BENSpm), respectively. Pharmaceutical formulations that contain a combination of the inhibitor of the methionine salvage pathway and a polyamine analogue are included, as are kits that contain such agents.

11 Claims, 16 Drawing Sheets

A

C

| Treatment conditions | | | | | |
|---|---|---|---|---|---|
| MTDIA | − | − | − | + | + |
| MTA | − | 10 | 20 | − | 20 |

MTAP
1.00  0.96  0.84  0.70  0.46

SMS
1.00  1.01  0.99  0.94  0.87

SRM
1.00  0.55  0.66  0.78  0.56

B-actin

FaDu

MTAP
1.00  0.88  0.75  1.66  2.03

SMS
1.00  1.46  0.99  2.09  2.04

SRM
1.00  1.51  1.84  2.79  3.98

B-actin

LNCaP

MTAP
1.00  1.75  2.17  2.98  2.66

SMS
1.00  1.31  1.39  1.50  0.94

SRM
1.00  1.00  1.41  1.32  1.06

B-actin

DU145

COMPOSITIONS AND METHODS FOR THERAPY OF PROSTATE CANCER USING DRUG COMBINATIONS TO TARGET POLYAMINE BIOSYNTHESIS AND RELATED PATHWAYS

CROSS-REFERENCE TO RELATED APPLICATIONS

This application claims priority to U.S. Provisional Application No. 62/163,353, filed on May 18, 2015, the disclosure of which is incorporated herein by reference.

STATEMENT REGARDING FEDERALLY SPONSORED RESEARCH OR DEVELOPMENT

This invention was made with government support under grant CA197996 awarded by the National Institutes of Health. The government has certain rights in the invention.

FIELD

This disclosure relates generally to treating prostate conditions.

BACKGROUND OF THE INVENTION

Prostate Cancer (CaP) is the second leading cancer causing mortality in men in the US [Jemal, A., et al, 2008. CA Cancer J Clin 58, 71-96 (2008)]. The cornerstone of clinical management of men presenting with advanced prostate cancer is androgen deprivation therapy (ADT), and this has been the case for over 70 years [Grivas, P. et al. Crit Rev Oncol Hematol 85, 82-93 (2013)]. ADT leads to remission in about 80% of the patients, but ultimately results in recurrent tumors (ADT recurrent prostate cancer (ADT-RCaP)) after 18-24 months. ADT-RCaP is characterized by alterations of the androgen axis which allow for continued androgen signaling even after ADT. The crucible of ADT drives the 'evolution' of CaP to survive the apoptotic signals caused by ADT and eventually overcome the anti-proliferative signals in the androgen deprived environment, ultimately resulting in a highly aggressive and therapy resistant version of the disease. Development of therapeutic strategies to 1) better treat recurrent disease, and 2) enhance the efficacy of ADT by reducing the ability of cells to survive ADT and thereby prevent recurrence would be of great clinical significance. Furthermore, there is an ongoing and unmet need for treating other prostate conditions, including androgen sensitive prostate cancer (AS-CaP) and benign prostate hyperplasia (BPH). The present disclosure is pertinent to these needs.

BRIEF SUMMARY

The present disclosure relates in part to the discovery that the high level of polyamine biosynthesis in prostate cancer (CaP) places strain the methionine cycle, which makes prostatic epithelial cells highly sensitive to perturbation of such metabolic pathways. The polyamine biosynthesis is driven by spermidine/spermine N1-acetyltransferase (SAT1). The methionine salvage pathway provides a means of mitigating this strain by recycling the one-carbon unit lost to polyamine biosynthesis. This process is compromised in many types of cancer by deletion of the methylthioadenosine phosphorylase (MTAP), but deletion of MTAP is very infrequent in CaP. The present disclosure relates to combination pharmacological approaches that in embodiments increases metabolic stress of CaP cells using a polyamine analogue to upregulate polyamine catabolism by increasing SAT1 activity, while concurrently reducing the cells' ability to mitigate that stress by inhibiting the activity of MTAP.

In one implementation the disclosure thus provides a method for inhibiting growth of prostate cancer (CaP) in an individual comprising administering to the individual i) an inhibitor of methionine salvage pathway in prostate of the individual and ii) a polyamine analogue. In embodiments the individual has been diagnosed with, or is suspected of having androgen sensitive prostate cancer (AS-CaP) or Castration recurrent CaP (CR-CaP). In one approach, the inhibitor of the methionine salvage pathway is an inhibitor of MTAP, and the polyamine analog that upregulates polyamine catabolism does so by increasing SAT1 activity. In certain implementations the inhibitor of the methionine salvage pathway comprises methylthio-DADMe-Immucillin (MTDIA), and/or the polyamine analogue comprises 1),N(11)-bisethylnorspermine (BENSpm). In embodiments the combination approach results in inhibition of prostate growth that is additive, or comprises a synergistic inhibition. In certain embodiments the disclosure is pertinent to individuals who are in need of treatment for a prostate condition, and may have or may be at risk for developing benign prostate hyperplasia (BPH). As a consequence of the combination treatment, the size of the prostate gland in the individual is reduced.

In another aspect the disclosure provides pharmaceutical formulations for use in treating a prostate condition in an individual, the formulations comprising i) an inhibitor of the methionine salvage pathway and ii) a polyamine analogue, as such agents are described above. Kits comprising the pharmaceutical formulations for such uses are also included.

BRIEF DESCRIPTION OF THE DRAWINGS

For a fuller understanding of the nature and objects of the invention, reference should be made to the following detailed description taken in conjunction with the accompanying drawings, in which.

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure relates in some aspects to the observation that the extraordinary level of polyamine biosynthesis found in prostate cells, and accentuated in prostate cancer (CaP), places strain on one-carbon metabolism and the methionine cycle making prostatic epithelial cells highly sensitive to perturbation of these metabolic pathways. The high level of polyamine biosynthesis is driven by the activity of spermidine/spermine N1-acetyltransferase (SAT1), which acetylates the polyamines leading to their secretion into the lumen, and necessitates de novo synthesis of polyamines to maintain intracellular levels. The methionine salvage pathway (MSP) provides a means of mitigating this metabolic strain by recycling the one-carbon unit lost to polyamine biosynthesis back into the methionine cycle, thereby replenishing s-adenosylmethionine (SAM) pools and protecting nucleotide pools. While this pathway is compromised in many types of cancer by deletion of the methylthioadenosine phosphorylase (MTAP) gene (located within 100 kb of the p16 locus), but deletion of MTAP is very rare in CaP. Thus, and without intending to be constrained by any particular theory, the present disclosure relates to pharmacologically increasing polyamine biosynthetic flux and the associated stress by upregulating SAT1 activity, while at the same time interfering with the cells' ability to mitigate the stress by inhibiting the MSP. Accordingly, in certain approaches the instant disclosure comprises a combination pharmacological approach to treating prostate conditions. In one non-limiting implementation, the disclosure relates to a combination pharmacological approach that increases metabolic stress of CaP cells by treating with a polyamine analogue to upregulate polyamine catabolism by increasing SAT1 activity, while at the same time reducing the cells' ability to mitigate that stress by inhibiting MTAP. In certain aspects this results in enhancing the extent and/or duration of clinical benefit of androgen deprivation therapy (ADT), but the approaches provided by the present disclosure are expected to be applicable to all types and stages of prostate cancer as described further below.

Figure 1:
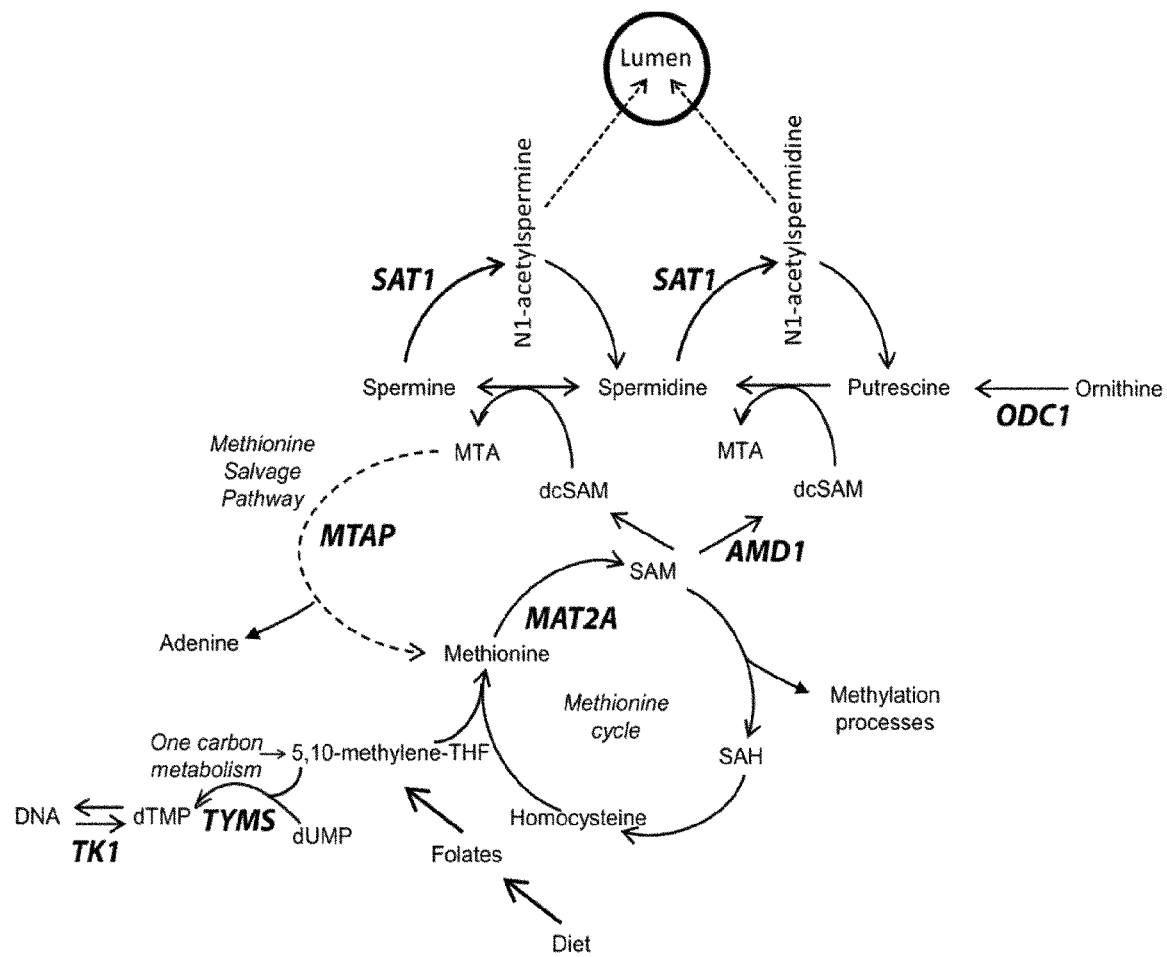
FIG. 1 provides an overview of methionine cycle, polyamine biosynthesis and the methionine salvage pathway. Key enzymes are bold. MTAP, Methylthioadenosine phosphorylase; SAT1, spermidine/spermine N1-acetyltransferase; MAT2A, methionine adenosyltransferase II alpha; AMD1, s-adenosylmethionine decarboxylase; ODC1, ornithine decarboxylase; TYMS, thymidylate synthase; TK1, thymidine kinase FIG. 2. Analysis of SAM and SAH pools in vivo and in vitro. A. SAM, SAH and SAM:SAH ratios in the liver, normal and diseased prostate of TRAMP mice fed a folic acid control diet as measured by HPLC. Statistical analyses compare each of the three tissues to one another using a One-Way Anova with Tukey correction. B. SAM, SAH and SAM:SAH ratios in the liver, normal and diseased prostate of TRAMP mice fed a folic acid control (con) and deficient (del) diet. SAM:SAH ratios are decreased in the liver and increased in the diseased prostate of TRAMP mice fed a folic acid deficient diet. Statistical analyses were made using an unpaired student t-test. C. SAM and SAH measurements and MTAP expression by real time RT-PCR in TRAMP derived C2G cell line following folate depletion, relative to control. SAM pools were correlated to MTAP expression levels in the XY-scatter plot. Statistical analyses for MTAP expression compares folate control and deplete conditions using an unpaired student t-test; correlation calculated by 2-tailed Pearson correlation test (*:p<0.05; :p<0.01; *: p<0.001; ****:p<0.0001).

In certain aspects, the combined approach comprises a synergistic inhibition of prostate cancer growth or progression of disease by combining MSP inhibition and enhancement of polyamine catabolism. Thus, aspects of this disclosure take advantage of an inherent metabolic strain accentuated in prostatic epithelial cells in order to develop the new therapeutic strategies described herein. These strategies leverage already existing metabolic strain by adding to it (increasing polyamine catabolism) while simultaneously blocking an important salvage pathway that helps to mitigate that strain (MTAP). In this regard, MTAP is the rate limiting enzyme involved in the methionine salvage pathway. The high degree of polyamine biosynthesis in prostate makes this salvage pathway important because decarboxylation of SAM is necessary to provide the propylamine donor required for generating spermidine and spermine, which also generates MTA as a by-product (see, for example, illustration in FIG. 1). The salvage pathway recycles MTA, which carries the one-carbon unit lost from the methionine cycle to polyamine biosynthesis, back to the methionine cycle (FIG. 1). MTA is a strong inhibitor of polyamine biosynthesis through end product inhibition of spermine and spermidine synthase (SMS and SRM, respectively). In the absence of MTAP, MTA can be released from the cell by passive diffusion, which avoids the inhibition of SMS and SRM, but wastes one-carbon units. The activity of MTAP not only optimizes elimination of MTA, but also reclaims adenine and methionine. The methionine can then be used to replenish SAM pools through the action of Methionine Adenosyltransferase II, Alpha (MAT2A).

Figure 2:
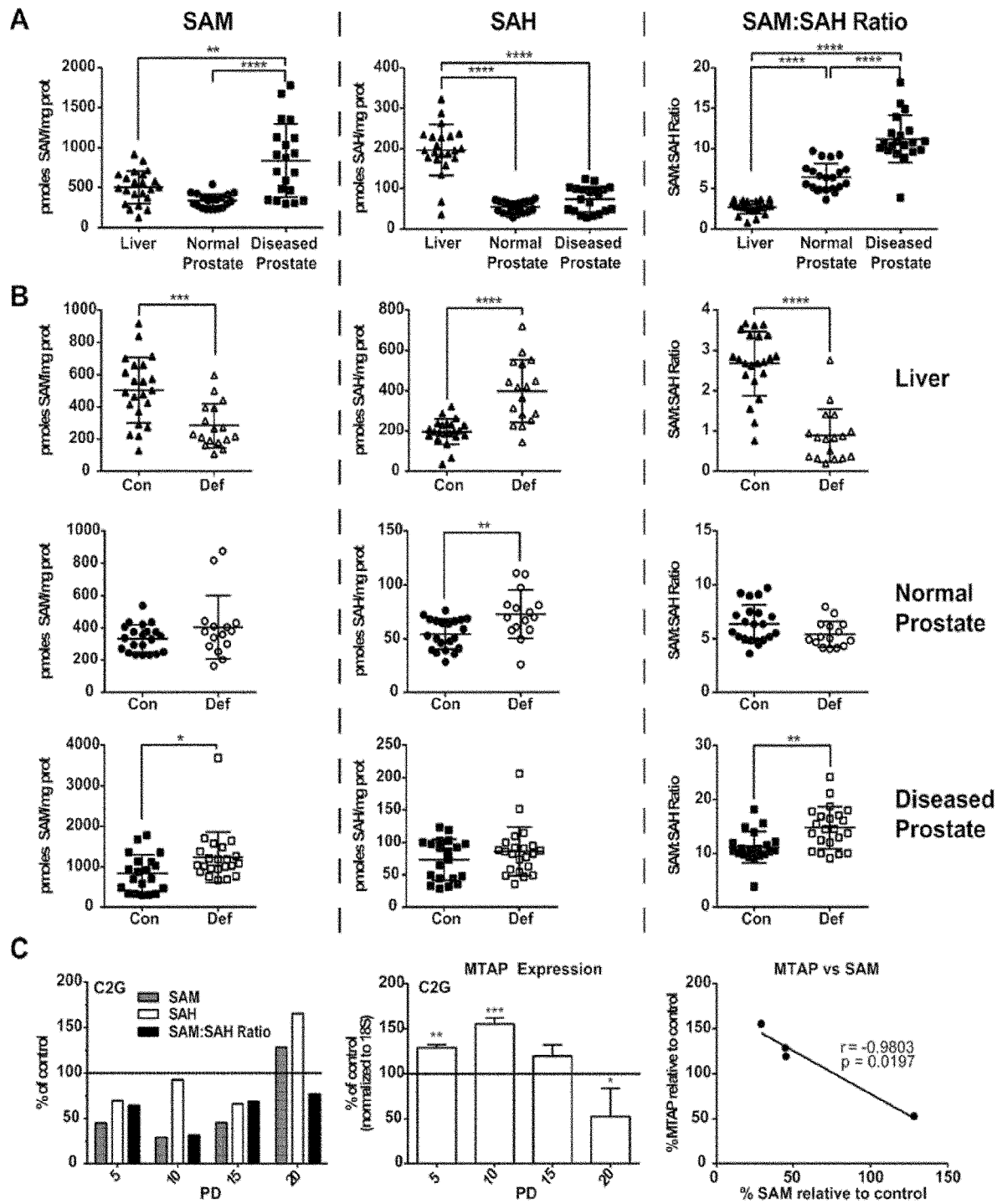

De novo synthesis of methionine depends on folate, which is acquired from the diet. Because of its characteristically high level of polyamine biosynthesis, prostate has a higher dependency on folate relative to other tissues, which is reflected in a higher flux of one-carbon units through one-carbon metabolism and the methionine cycle. In connection with this, we determined that normal prostate and diseased prostate maintain a ~2.5 times and ~4 times higher basal SAM to SAH ratio than the liver (FIG. 2A). Unexpectedly, upon folate deficiency in mice, normal prostate and diseased prostate maintain a ~6 times and ~16.5 times higher SAM to SAH ratio than the liver (FIG. 2B). Interestingly, we found that the TRAMP C2G prostate cancer cell line exhibited a drop in SAM pools upon folate deficiency, but that by 20 population doublings (PDs) the SAM pools recovered and this correlated with increased expression of MTAP while SAM pools were low (FIG. 2C). These indicate that MTAP is important for CaP to maintain SAM pools under conditions of metabolic stress.

MTAP is one of the genes most frequently deleted in some types of cancer, likely due to its proximity to the CDKN2A/p16 locus. This suggests that losing p16 gives cancer cells a greater growth advantage than retaining MTAP. It may be the case that deletion of MTAP is less harmful in cell types with relatively low flux through polyamine biosynthesis, the methionine cycle, and one-carbon metabolism, but this does not seem to be the case for CaP cells. We determined that the MTAP gene is rarely deleted (14 of 1543 cases) across publically available datasets for CaP, as well as in a panel of CaP cell lines and patient samples. We also show here for the first time disrupting the function MTAP can significantly block CaP xenograft growth in nude mice. In addition, dietary folate supplementation was able to partially rescue this growth inhibition, suggesting that at least part of the antiproliferative effect is related to metabolic deficits that can be corrected by higher intake of folate. Pharmacological inhibition of MTAP in the drinking water also resulted in a significant block in CaP xenograft growth, making use of MTAP inhibitors represents a novel therapeutic approach to treating CaP. When combined with an agent that upregulates the activity of SAT1 it is expected that the disclosure will provide a synergistic inhibition of prostate cancer growth in individuals in need thereof.

In view of the foregoing it will be recognized that in certain embodiments, the present disclosure comprises methods for treating a prostate condition in individuals in need thereof which generally comprise administering to the individual a combination of i) an inhibitor of the methionine salvage pathway, or ii) a polyamine analogue, or a combination thereof. Combinations are used to obtain an additive or greater than additive effect. Pharmaceutical compositions comprising an inhibitor of the methionine salvage pathway and a polyamine analogue are included. The disclosure is illustrated in certain embodiments using the polyamine analogue N(1),N(11)-bisethylnorspermine (BENSpm) and the MTAP inhibitor methylthio-DADMe-Immucillin (MT-DIA), but other polyamine analogues and MTAP inhibitors may be substituted. In certain embodiments the polyamine analogue is selected from alpha-difluoromethylornithine (DFMO), PG-11047, $N^1$-ethyl-$N^{11}$-[(cyclopropyl)methyl]-4,8,-diazaundecane (CPENSpm). In embodiments, aspirin may be used.

In certain approaches, the individual in need has been diagnosed with, is suspected of having, or is at risk for developing the prostate condition, wherein the prostate condition is selected from benign prostate hyperplasia (BPH), androgen sensitive CaP (AS-CaP) Castration recurrent CaP (CR-CaP), or prostatic intraepithelial neoplasia (PIN), including but not limited to high grade PIN. In certain approaches, the individual is determined to have a Gleason score of at least 6 based on a prostate biopsy. In certain embodiments, the individual is diagnosed with a stage of prostate cancer that is Stage T1-4, or Stage N0-3, or Stage M0, or M1.

In an embodiment, the disclosure comprises administering to an individual with prostate cancer an effective amount of the polyamine analogue and the MTAP inhibitor such that growth of the prostate cancer is inhibited. The disclosure includes administering such combinations to individuals whose prostate cancer is androgen sensitive. The disclosure also comprises administering the combinations to an individual who has developed resistance, or is at risk for developing resistance, to anti-androgen or anti-androgen receptor (AR) agents (broadly termed "androgen deprivation therapy"), or other chemotherapeutic agents. In certain aspects, the individual has a form of prostate cancer that is resistant to a non-steroidal anti-androgen agent, or is resistant to a steroidal anti-androgen agent.

In certain embodiments, the disclosure comprises selecting an individual who has been diagnosed with any of the aforementioned forms of prostate cancer and administering to the individual an effective amount of the combination of the MTAP inhibitor and the polyamine analog.

In an embodiment the disclosure comprises testing to determine if an individual has a particular form of prostate cancer that is either sensitive, or resistant to one or more anti-androgen or anti-AR drugs and, subsequent to determining administering to the individual the combination of the MTAP inhibitor and the polyamine analog.

Various methods known to those skilled in the art may be used to introduce the compositions of the invention to an individual. These methods include but are not limited to intradermal, intramuscular, intraperitoneal, intravenous, subcutaneous, oral, intranasal and intra-tumoral routes. It will be recognized by those of skill in the art that the form and character of the particular dosing regimen employed in the method of the invention will be affected by the route of administration and other well-known variables, such as the size, age and overall health of the individual, and the stage and type of the particular stage of prostate condition being treated. Based on such criteria, and given the benefit of this disclosure, one skilled in the art can determine an effective amount of a combination of MTAP inhibitor and the polyamine analog to administer to an individual. In one embodiment, the MTAP inhibitor comprises MTDIA and is administered in an amount of about 21 mg/kg, up to 1,000 mg/kg/day for a period of time, such as for one or more seven-day intervals. In certain embodiments the polyamine analog comprises BENSpm and is administered in an amount of from 25-74 mg/kg. In certain embodiments BENSpm or another polyamine analogue is administered weekly or twice a week and/or with a drug holiday, i.e, a structured or strategic treatment interruption. In certain implementations BENSpm may be administered using a dosing schedule of 100 mg/M$^2$/day for five days to 185 mg/M$^2$/day for five days, and such schedule may be repeated.

In embodiments, inhibition of prostate cancer growth comprises a reduction in tumor size, and/or an inhibition of metastasis and/or the formation of metastatic foci, and/or an extension of the life span of an individual diagnosed with prostate cancer relative to an individual who does not receive the combination treatment.

The method of the invention can be performed in conjunction with conventional anti-cancer therapies. Such therapies can include but are not limited to known chemotherapies and anti-prostate cancer approaches, such as androgen deprivation therapy, surgical interventions, and radiation therapy. The combination of the MTAP inhibitor and the polyamine analog could be administered prior to, concurrently, or subsequent to such anti-cancer therapies. Likewise, the combination can be administered prior to, or subsequent to, or concurrently with any other chemotherapeutic agent. Administering the combination comprises administering each agent so that they are both present in the individual at the same time and can exert their mutual functions in the prostate. It will thus be recognized that the agents can be administered concurrently or sequentially, so long as the desired effect is achieved. In certain embodiments, the combination of the MTAP inhibitor and the polyamine analog is administered to an individual who has been previously and unsuccessfully treated with an anti-androgen agent(s) and/or anti-androgen approach, such as castration, whether chemically or surgically performed. In embodiments, the MTAP inhibitor and the polyamine analog are administered with and/or to enhance the effect of another chemotherapeutic agent, non-limiting examples of which include Radium-223, such as for men with prostate cancer that has metastasized to bone, docetaxel, sipuleucel-T, such as for men who have few or no symptoms produced by the prostate cancer, cabazitaxel, such as for men with prostate cancer that has worsened while receiving docetaxel, mitoxantrone, bicalutamide, Enzalutamide, ARN-509, ODM-201, flutamide, nilutamide, 5α-reductase inhibitors (Finasteride, Dutasteride), LHRH receptor agonists (e.g., Leuprolide, Goserelin, triptorelin), LHRH antagonists (e.g., Abarelix), Ketoconazole, low-dose corticosteroids, i.e., prednisone, and combinations thereof.

In certain aspects the inhibitor of the methionine salvage pathway and the polyamine analogue can be provided as a pharmaceutical formulation by combining both agents with a standard pharmaceutically acceptable carrier or excipient, diluent, etc. Some examples of such reagents can be found in: *Remington: The Science and Practice of Pharmacy* (2005) 21st Edition, Philadelphia, Pa. Lippincott Williams & Wilkins. Pharmaceutical formulations can be provided in a form that is suitable for use with any of the aforementioned delivery routes, including but not necessarily limited to liquids, capsules, tablets, softgels, powders for reconstitution, ampules, pre-loaded containers, etc.

In another aspect the disclosure includes an article of manufacture, such as a kit, comprising packaging material and the inhibitor of the methionine salvage pathway and the polyamine analogue, wherein the pharmaceutical composition is effective for use treating a prostate condition as described herein, and wherein the packaging material optionally comprises a label or other printed material which provides an indication that the agents can be used in methods as described herein, such as for treating a prostate condition. The kit can contain one or more containers, and may be provided with the inhibitor of the methionine salvage pathway and the polyamine analogue in separate containers, such as for mixing together prior to use, or for sequential administration, or the inhibitor of the methionine salvage pathway and the polyamine analogue can be in the same container, such as in a ready-to-use pharmaceutical formulation.

The following Examples are intended to illustrate various embodiments of the disclosure, but are not intended to be limiting.

EXAMPLE 1

SAM Pools are Protected in Prostate Cancer Both In Vitro and In Vivo

Transgenic Adenocarcinoma of Mouse Prostate (TRAMP) mice were fed control folate defined diets from weaning until mice were sacrificed at 12 weeks of age. This model is driven by the prostate specific expression of SV40 large- and small-T-antigen upon puberty. The anterior prostate has very limited expression of the transgene and is generally free of pathology at 12 weeks of age. The dorsal, lateral and ventral lobes, however, highly express the transgene and by 12 weeks of age often exhibit high grade PIN or adenocarcinoma. We used the anterior prostate from 12 week old mice as an approximation of normal prostate and took diseased tissue from the dorsal, lateral and ventral prostate. Analysis of SAM pools by HPLC in the liver, anterior prostate, and diseased prostate demonstrate that SAM levels are significantly higher in the diseased prostate when compared to the anterior prostate and liver (FIG. 2A). Conversely, S-adenosylhomocysteine (SAH) levels are significantly lower in both the anterior and diseased prostate when compared to the liver, which results in a significantly higher SAM:SAH ratio (FIG. 2A). Thus, in control conditions, the basal SAM to SAH ratios are ~2.5 times and ~4 times higher in the normal prostate and diseased prostate, respectively, than the liver.

TRAMP mice were also fed folate deficient diets from weaning until mice were sacrificed at 12 weeks of age. It is known that folate deficiency leads to decreased SAM pools, as well as nucleotide pools. Analysis of SAM pools in the liver of TRAMP mice demonstrates that dietary folate deficiency had a significant effect on SAM and SAH levels (FIG. 2B). Specifically, folate deficiency induced a significant decrease in SAM pools and a significant increase in SAH, resulting in a significant decrease in the SAM:SAH ratio (FIG. 2B—top panels). Conversely, we detected no change in the SAM:SAH ratio in the normal prostate (FIG. 2B—middle panels). Strikingly, SAM levels in the diseased prostate were significantly higher in the deficient diet resulting in a significantly higher SAM to SAH ratio, opposite of what was predicted and seen in liver (FIG. 2B—bottom panels). Notably, in mice fed a folate deficient diet, the SAM to SAH ratio is ~6 times and ~16.5 times higher in normal prostate and diseased prostate, respectively, than in the livers of the same mice.

When TRAMP C2G prostate cancer cells are grown in 100 nM FA, SAM and SAH pools are depleted compared to control as early as PD 5 (FIG. 2C). This depletion is maintained through PDs 10 and 15, but rebounds at PD 20 (FIG. 2C). This suggests the prostate has an inherent mechanism to protect SAM even under stressful conditions. We tested whether the methionine salvage pathway, controlled by the rate-limiting enzyme MTAP, may play an important role. Real time RT-PCR analysis of MTAP in TRAMP C2G cells showed that while SAM pools were depleted through PD15, MTAP expression was significantly upregulated compared to control (FIG. 2C). Once SAM pools recovered by PD20 MTAP expression was significantly downregulated compared to the control (FIG. 2C). SAM levels and MTAP expression levels were found to significantly and inversely correlate across population doublings 5-20 under folate restricted conditions (FIG. 2C). These data suggest that MTAP is upregulated to compensate for the SAM pool depletion and may therefore be vital for maintaining growth in this metabolically strained environment.

EXAMPLE 2

MTAP Expression is Retained in Both CaP Cell Lines and CaP Patients.

Figure 3:
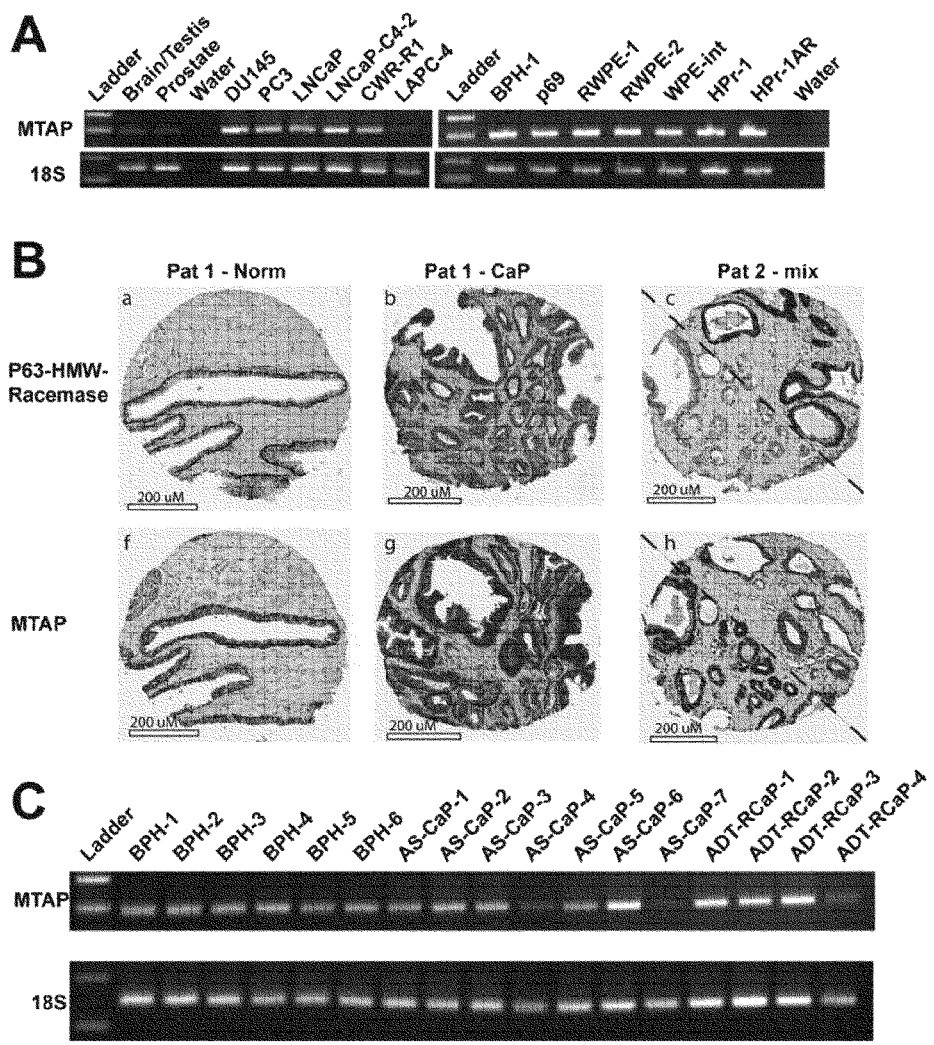
FIG. 3: MTAP expression is conserved in normal prostate and prostate cancer. A. Semiquantitative RT-PCR results (28 cycles) measuring 18S and MTAP in human brain/testis, human prostate, and 13 human prostate cell lines. B. Immunohistochemistry against P63-HMW-Racemase (top) and against MTAP (bottom) from a tissue microarray of 66 human prostate cancers and normal adjacent tissue. Representative cores are shown. In the top panels, brown staining indicates normal ducts or PIN; red staining indicates adenocarcinoma. MTAP staining is shown as brown staining in the bottom panels. Patient 1 has individual cores of normal (a and f) and cancer (b and g). Patient 2 (c and h) displays a mix of normal ducts/PIN and adenocarcinoma on either side of the diagonal. C. Semi-quantitative RT-PCR results (28 cycles) measuring 18S and MTAP in human benign prostatic hyperplasia (BPH), androgen sensitive CaP (AS-CaP), and androgen deprivation therapy recurrent CaP (ADT-RCaP).

If MTAP is required for prostate cancer to maintain growth, it would be expected that CaP would retain the MTAP locus despite its close proximity to the commonly deleted p16 locus. The TCGA provisional data set on CaP indicated homozygous deletion of MTAP in only 2 out of 498 cases. In the Memorial Sloan Kettering data set, MTAP deletion was seen in 3 out of 216 cases [Taylor B S, et al. Cancer Cell. 2010; 18:11-22]. In the Stand Up to Cancer/ Prostate Cancer Foundation Dream Team metastatic CaP dataset deletion was seen in 1 out of 150 cases. Overall, of the 9 publically available datasets, MTAP deletion was present in only 14 of 1543 total cases (www.cbioportal.org). This is in contrast to a number of studies in other cancer types that found deletion and/or mutation of MTAP at high frequency in: glioblastoma (GBM) 151/273 cases [Network TCGAR. Comprehensive genomic characterization defines human glioblastoma genes and core pathways. Nature. 2008; 455:1061-1068]; bladder urothelial carcinoma 39/127 cases [Network CGAR. Comprehensive molecular characterization of urothelial bladder carcinoma. Nature. 2014; 507:315-322], and in lung squamous cell carcinoma 46/178 cases [Network TCGAR. Comprehensive genomic characterization of squamous cell lung cancers. Nature. 2012; 489:519-525]. mRNA expression by semi-quantitative RT-PCR (28 cycles) in a panel of 13 human prostate cell lines (both transformed and non-transformed) confirmed strong MTAP expression in all, regardless of androgen sensitivity or AR status (FIG. 3A). Fluorescence in situ hybridization (FISH) using probes specific for either the MTAP or p16 loci on a human tissue microarray (TMA) comprised of prostate tissue from 75 patients indicated no cases of homozygous deletion at either locus (data not shown). Only 2 out of 75 patients exhibited a monoallelic deletion of the region of interest. MTAP expression analysis by immunohistochemistry on the same TMA confirmed that MTAP expression was detectable in 65 out of 66 cases (FIG. 3B). No significant difference was observed in high or low MTAP staining comparing matched normal tissue to cancer. MTAP staining intensity and percent positive cells did not correlate with Gleason score.

Figure 7:
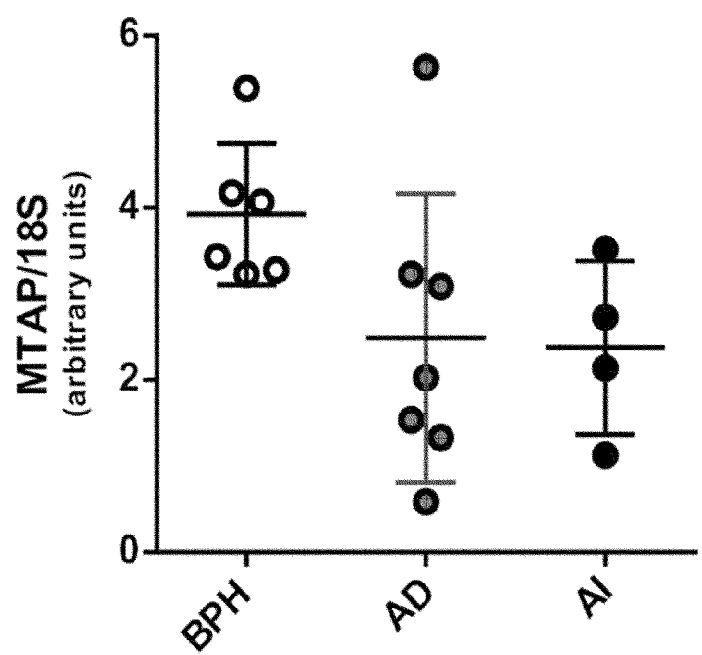
FIG. 7. MTAP expression in human prostate cancer. No significant trend was seen in relation to stage of disease and MTAP expression in tissues representative of BPH, AS-CaP, and ADT-RCaP as measured by RT-PCR.

To assess if MTAP expression was lost or changed during the process of CaP recurrence after androgen deprivation therapy (ADT), RNA was isolated from 6 samples of benign prostatic hyperplasia (BPH), 7 samples of androgen stimulated CaP (AS-CaP), and 4 samples of ADT-recurrent CaP (ADT-RCaP). MTAP expression was retained at all stages (FIG. 3C) as shown by semi-quantitative RT-PCR (28 cycles). Real-time RT-PCR found no significant trend of increased or decreased expression from BPH, to AS-CaP, to ADT-RCaP (FIG. 7). These data demonstrate that the MTAP locus and expression are retained in CaP, regardless of cancer stage and/or patient androgen status, consistent with the idea that retention of MTAP might indeed be pivotal in sustaining CaP growth.

EXAMPLE 3

MTAP Contributes to CaP Growth In Vitro and In Vivo

Figure 9:
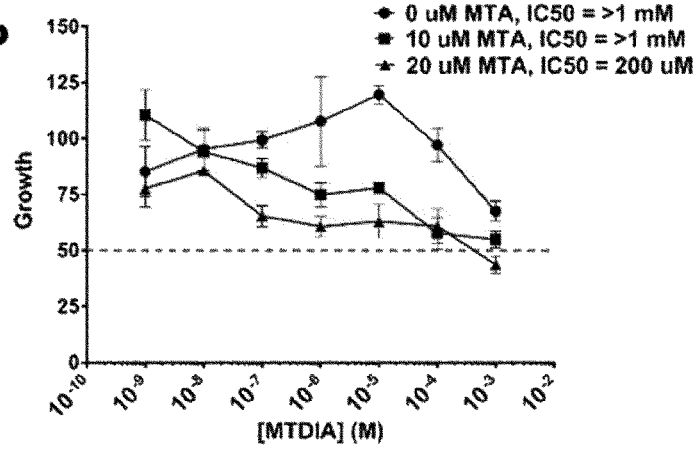
FIG. 9. (A) Proliferation curves for LNCaP, DU145 and PC3 treated with MTDIA in the absence or presence of 10 or 20 uM MTA, for 4 and (B) 8 days. Results of biological triplicates are shown with absolute IC50s indicated for each condition. (C) Western blot analysis of FaDu, LNCaP, and DU145 cells after indicated treatments of MTA (0, 10, or 20 uM) or the respective 4 day IC25 and IC50 dose of MTDIA for each cell line plus or minus MTA immunoblotted with antibodies against MTAP, SMS, and SRM, with B-actin as a loading control. Western blot images are representative of biological triplicates. Band intensity values normalized to B-actin relative to control conditions are indicated below the respective band.
Figure 9:
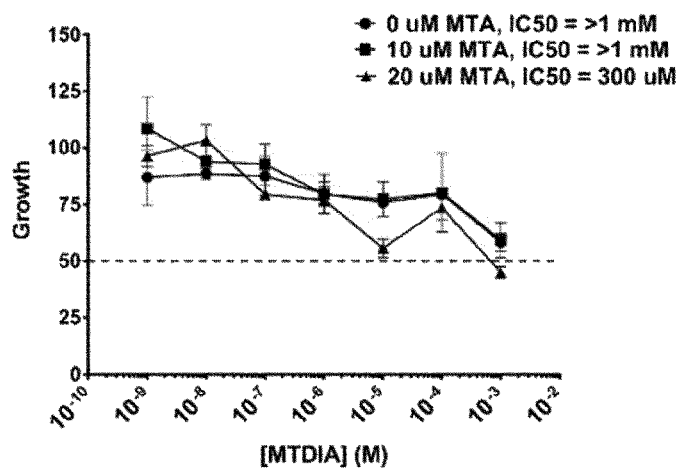
Figure 9:
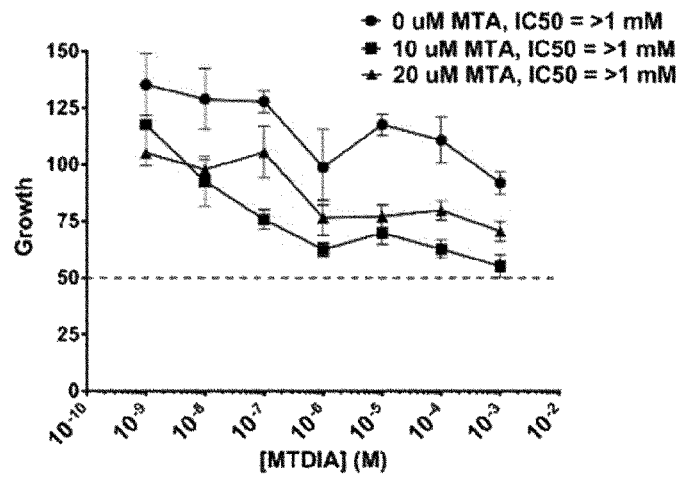
Figure 9:
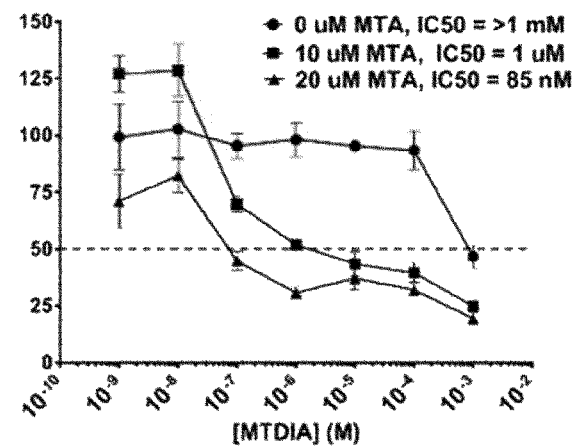
Figure 9:
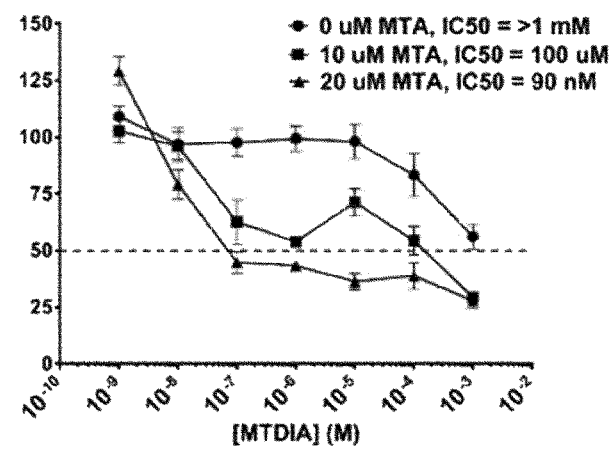
Figure 9:
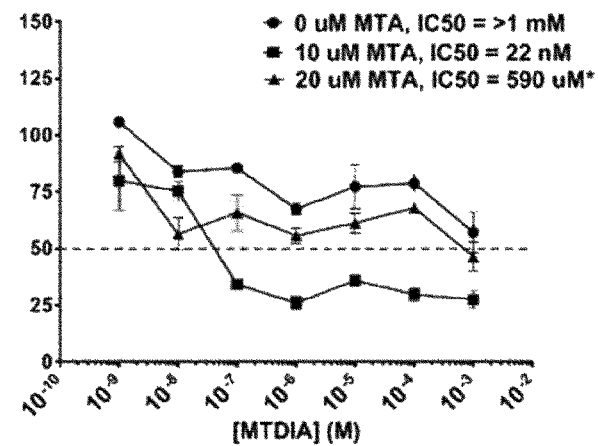
Figure 9:
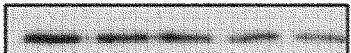
Figure 9:
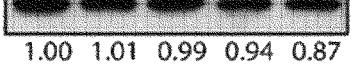
Figure 9:
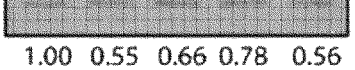
Figure 9:
Figure 9:
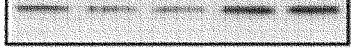
Figure 9:
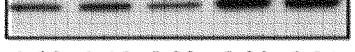
Figure 9:
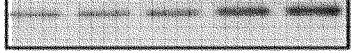
Figure 9:
Figure 9:
Figure 9:
Figure 9:
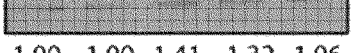
Figure 9:

To study MTAP contribution to CaP growth we used RNA interference to generate pure populations of LNCaP clones with stably silenced MTAP. We tested four shRNA sequences against MTAP (A-D) and found that both B and D were effective at significantly reducing MTAP protein (FIG. 4A). Individual cells were isolated to create clonal populations of cells containing sequences B, D, and scrambled shRNA sequences predicted to target no proteins (shMTAP-B #1, shMTAP-D #1, shScr #1, and shScr #4). In vitro, LNCaP cells silenced for MTAP had growth rates comparable to control cells when grown in complete medium. Conversely, when grown under folic acid restricted with or without the addition of 20 µM MTA to the media. However, by 8 and 12 days there was a dramatic effect on cell growth for all three lines with the addition of 20 µM MTA, but little to no effect without it. In all three cell lines, the proliferation curves after 12 days of treatment show an IC50 of MTDIA>1 mM in the absence of MTA (FIG. 5B), but in the 10-100 nM range with the addition of 10 or 20 µM MTA. Table 1 shows the IC50 values for all three cell lines at 4, 8, or 12 days with and without the addition of MTA to the media. Nanomolar range IC50 values are highlighted. IC50 curves at 4 and 8 days of treatment are shown in FIG. 9. These data demonstrate that MTDIA is effective for blocking prostate cancer cell lines with 8-12 days of treatment in the presence of MTA.

TABLE 1

Table 1: IC50 values for MTDIA in prostate cancer cell lines

| | LNCaP | | | PC3 | | | DU145 | | |
|---|---|---|---|---|---|---|---|---|---|
| | 0 µM MTA | 10 µM MTA | 20 µM MTA | 0 µM MTA | 10 µM MTA | 20 µM MTA | 0 µM MTA | 10 µM MTA | 20 µM MTA |
| 4 days | >1 mM | >1 mM | 200 µM | >1 mM | >1 mM | 300 µM | >1 mM | >1 mM | >1 mM |
| 8 days | >1 mM | 1 µM | 85 nM | >1 mM | 100 µM | 90 nM | >1 mM | 22 nM | 590 µM |
| 12 days | >1 mM | 11 nM | 14 nM | >1 mM | 80 µM | 82 nM | >1 mM | 14 nM | 10 nM | conditions (100 nM folic acid), LNCaP cells silenced for MTAP, but not scrambled control cells, produced significantly fewer colonies when compared to the same cells grown in control medium (200 nM folic acid) (FIG. 4B). These results indicate that MTAP partial loss of function caused by shRNA alone is insufficient to cause defects in proliferation in vitro, but instead requires additional metabolic stress such as restrictive levels of folate availability.

Subcutaneous injection of either 106 LNCaP shScr #4 cells or 106 LNCaP shMTAP-D #1 in nude mice (n=20 per group) showed that indeed, MTAP knock down significantly ($p<0.0001$) prevented the formation of tumors in vivo (FIG. 4C). Dietary folate supplementation was able to partially rescue growth of LNCaP xenografts with MTAP knockdown (FIG. 4C solid circles), suggesting that at least part of the xenograft growth inhibition caused by loss of MTAP was associated with downstream metabolic effects that could be partially mitigated by folate supplementation. Combined, these genetic data suggest that MTAP is required for CaP to grow in vivo and that MTAP loss of function impinges on one-carbon metabolism and the methionine cycle.

EXAMPLE 4

Pharmacological Inhibition of MTAP Blocks Growth In Vitro and In Vivo

Figure 4:
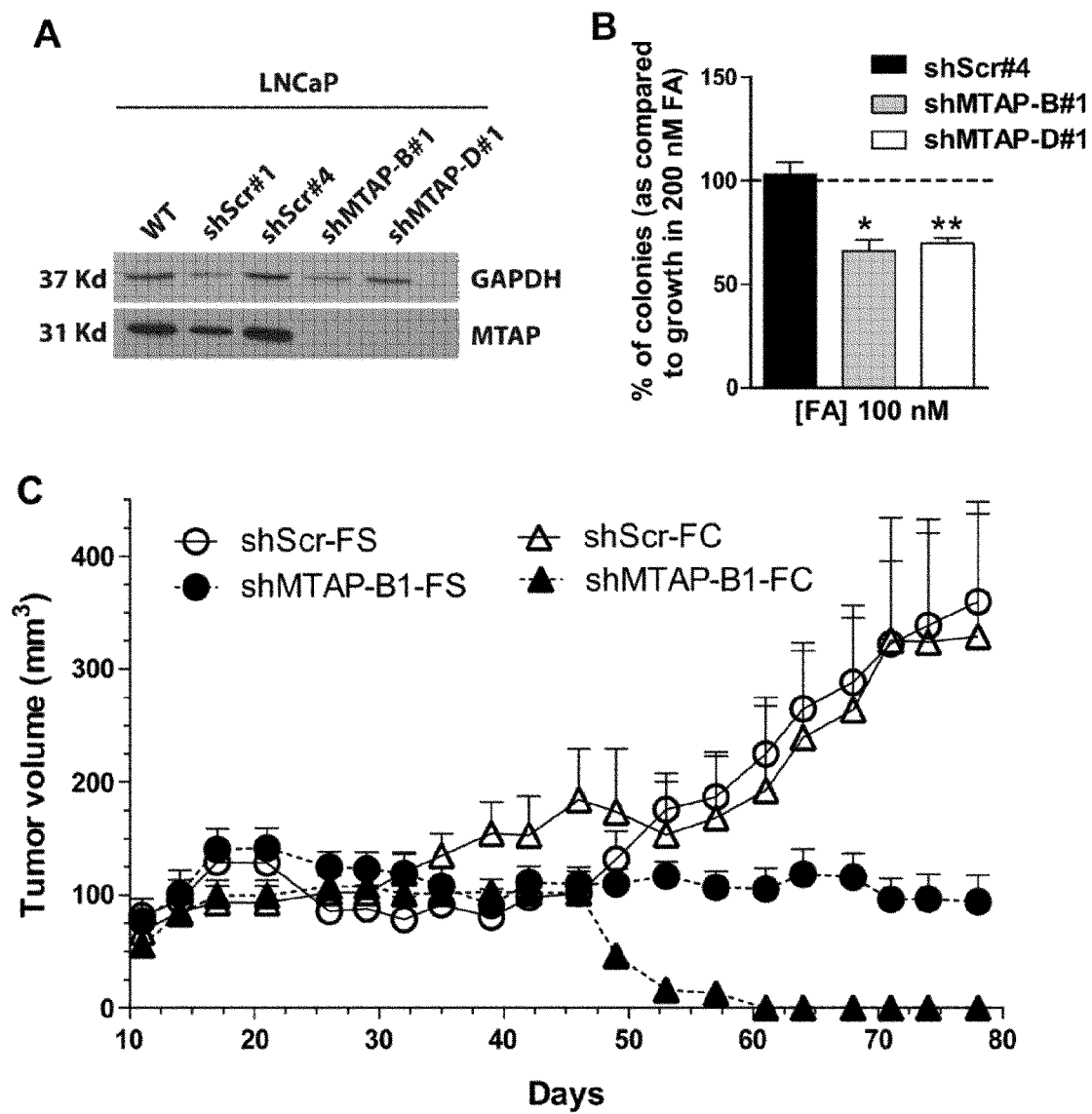
FIG. 4: RNA interference of MTAP inhibits prostate cancer growth in vitro and in vivo. A. Transfection with two shRNAs targeting MTAP (shMTAP-B #1 and D #1) in LNCaP cells decreases MTAP protein expression when compared to wild type or scramble control as measured by western blotting. B. Colony formation assay. Folic acid restricted conditions (100 nM) affects growth in LNCaP cells with MTAP knockdown or scrambled control shRNA compared to growth in 200 nM FA. Scrambled control cells are unaffected while both knockdown clones of MTAP show significantly reduced colony formation. *:p<0.05; **:p<0.01; t-test C. LNCaP xenograft growth in nude mice fed the folate control diet (FC—triangles) or a folate supplemented diet (FS—circles), with scrambled control (open symbols and solid lines) or MTAP shRNA (solid symbols and dashed line). $1 \times 10^6$ cells in matrigel were injected into 20 nude mice for both control and MTAP knockdown lines. On the control diet and the supplemental diet, MTAP knockdown significantly reduces xenograft growth, p<0.0001 and p=0.013, respectively; t-test. Folate supplementation partially rescues xenograft growth in knockdowns.
Figure 5:
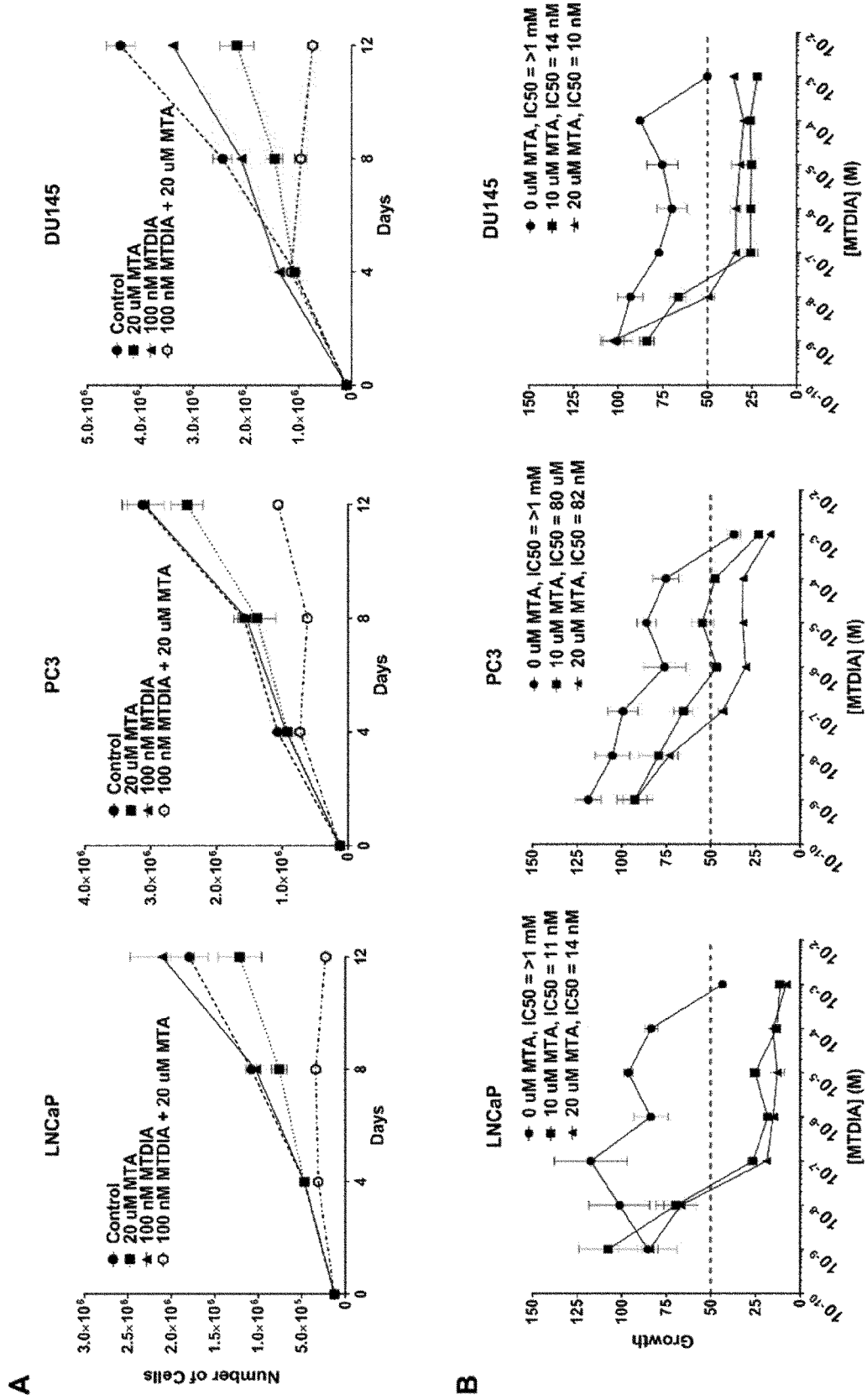
FIG. 5: Pharmacological inhibition of MTAP blocks prostate cancer growth in vitro and in vivo. A. Growth curves of 1 androgen sensitive (LNCaP), and 2 androgen insensitive cell lines (DU145 and PC3) treated with vehicle control, 100 nM MTDIA alone, 20 uM MTA, or 100 nM+20 uM MTA for 12 days. 125,000 cells/well in 6 well plates were plated, 24 hours later were refreshed with media containing 0, 10 or 20 uM MTA and treated with vehicle or 100 nM MTDIA, with drug and media replenished every 48 hours. Cells were trypsinized, counted by trypan blue exclusion and replated every 96 hours. Results of biological triplicates are shown. B. Proliferation curves after 12 days of treatment with MTDIA ranging in dose from 1 nM to 1 mM, in the absence or presence of 10 uM or 20 uM MTA. Absolute IC50s are indicated for each condition. C. LNCaP xenograft growth in nude mice. $1 \times 10^6$ wild type LNCaP cells in matrigel were injected into 60 nude mice. Twenty mice each were given the MTAP inhibitor MTDIA in the drinking water for a daily dose of either 9 mg/kg or 21 mg/kg, and 20 control mice were given no drug. Drug was removed on day 61 for the 21 mg/kg group, which was carried out to day 91. p<0.001 t-test.
Figure 5:
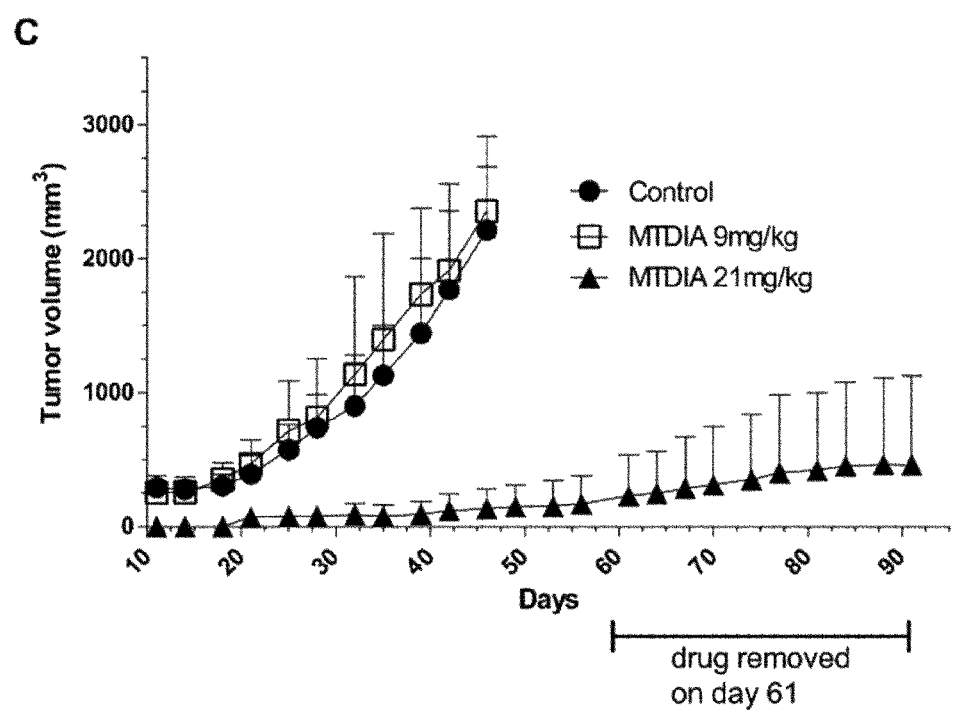
Figure 8A:
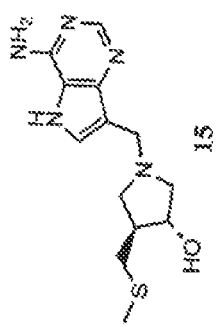
FIGS. 8A and 8B. Analytical data for (3R,4S)-1-[(9-Deaza-adenin-9-yl)methyl]-3-hydroxy-4-(methylthiomethyl)-pyrrolidine. A) 1H NMR and B) 13C NMR, and Mass Spectrum are consistent with structure 15 in the scheme shown in FIG. 6 and agree with similar data published previously (Compound 7 on page 4684 of J. Med. Chem., 2005, 48, 4679-4689)
Figure 8A:
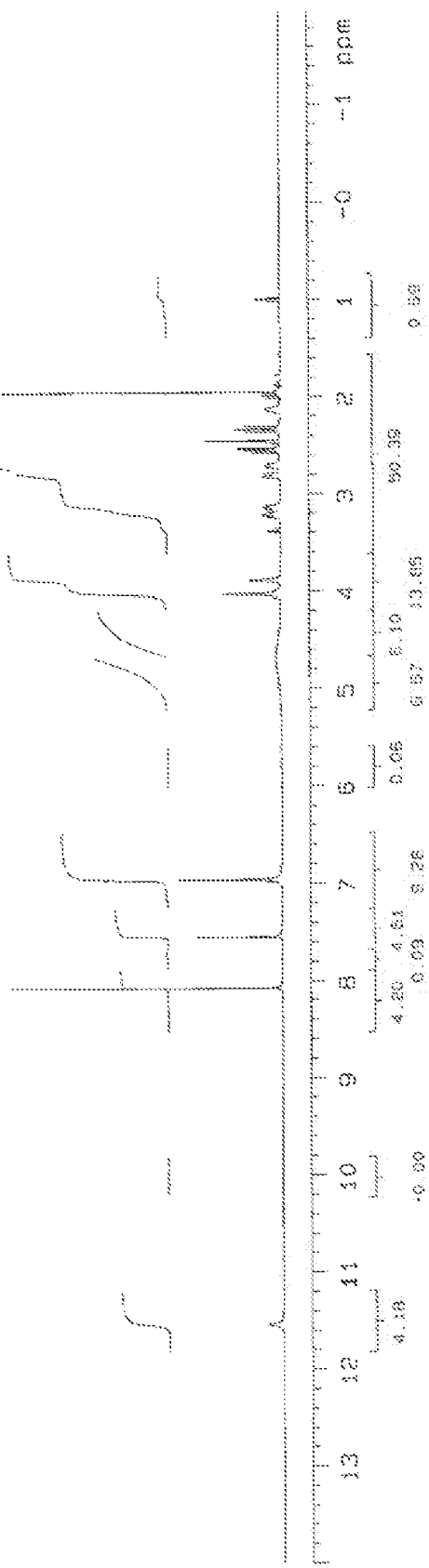
Figure 8B:
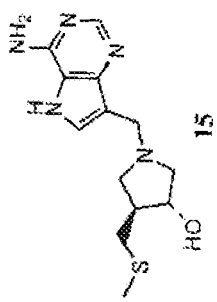
Figure 8B:
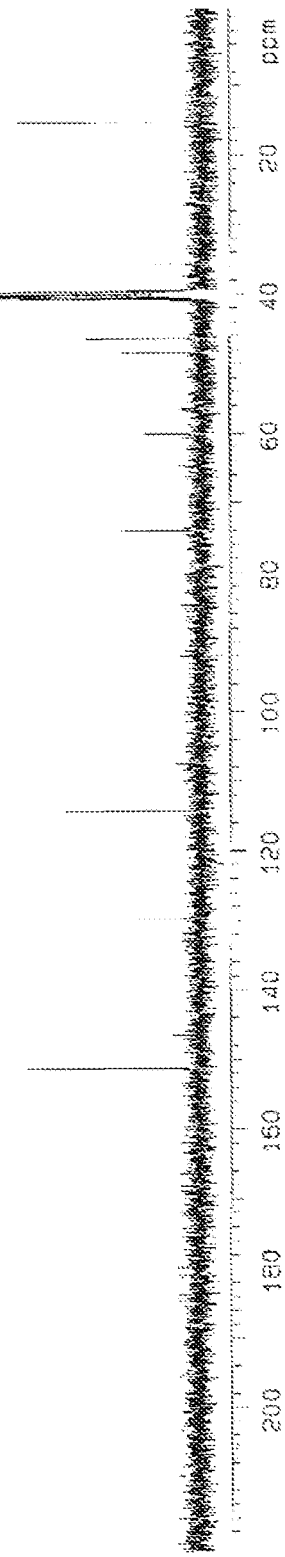

A transition state analog inhibitor of MTAP, Methylthio-DaDMe-Immucillin-A (MTDIA) was previously described and shown to be effective following a 6 or 12 day treatment at ~10 and 100 nM MTDIA when 20 uM MTA was added to the media in both lung adenocarcinoma cell lines and head and neck squamous carcinoma cell lines, respectively [Basu I, et al. J Biol Chem. 2007; 282:21477-21486; Basu I, et al. J Biol Chem. 2011; 286:4902-491]. 32]. We synthesized MTDIA and the analytical data on the synthesized compound are shown in FIGS. 8A and 8B with the scheme used for synthesis shown in FIG. 6. As shown in FIG. 5A, 4 days of 100 nM MTDIA treatment resulted in limited effects on growth for the LNCaP, PC3, and DU145 cell lines either We subcutaneously injected $10^6$ wild-type LNCaP cells on the right flank of nude mice (n=20 per group), and observed that treatment with 21 mg/kg MTDIA in the drinking water daily, caused a significant ($p<0.001$) block in xenograft growth when compared to the untreated control and the 9 mg/kg dose (FIG. 5C). In addition, upon drug removal at day 61 a significant block in xenograft growth was maintained (FIG. 5C). These data show that pharmacological inhibition of MTAP is effective at blocking androgen sensitive CaP growth in vitro and in vivo.

The IC50 of MTDIA for FaDu cells in the presence of 20 uM MTA was ~50 nM following only a 6 day treatment (data not shown). However, for LNCaP, PC3 and DU145 cells 6 days had no effect at blocking cell growth at low concentrations of MTDIA (data not shown). For CaP cell lines 8 days was needed to see an effect of MTDIA. To further evaluate this difference we investigated molecular differences between the head and neck cell line, FaDu, compared to LNCaP and DU145. In the presence of 10 and 20 uM MTA for 4 days, MTAP protein expression is slightly increased in DU145, while in FaDu it is slightly decreased as measured by western blot (FIG. 9C). MTAP levels are unchanged in LNCaP upon MTA treatment. Strikingly, upon treatment with each cell line's respective IC25 and IC50 of MTDIA in the presence or absence of MTA, FaDu downregulates MTAP while both CaP cell lines upregulate expression of MTAP. In addition, spermine synthase is downregulated in FaDu cells upon treatment with MTDIA, but upregulated in LNCaP cell lines. These Western blot results were reproducible in biological triplicate experiments. This suggests that there are inherent mechanistic differences between the two types of cell lines in their ability to deal with accumulation of MTA, and that CaP cells can partially compensate for MTAP inhibition or increased MTA concentrations by upregulating both MTAP and spermine synthase in the initial stages of a 4 day treatment. Therefore, this could account for the cell line specific difference in length of time it takes to see MTDIA's effects. Nevertheless, MTDIA is highly effective and potent for blocking androgen-sensitive CaP growth in vitro following long-term treatments and in vivo.

EXAMPLE 5

Materials and Methods for the Foregoing Examples

Cell lines and human tissue procurement—TRAMP-C2G cells are a clonal CaP cell line derived from a TRAMP prostate tumor. The human prostate cancer cell lines WPE-int, DU145 and PC-3 were purchased from the American Tissue Type Collection (ATCC, Manassas Calif.). p-69 cells, LNCaP, LNCaP C4-2, CWR-R1, and LAPC-4 cells, the epithelial non-transformed CaP cell line RWPE-1 and the transformed version RWPE-2, and the head and neck squamous cell carcinoma cell line FaDu were available at the Roswell Park Cancer Institute. The human prostate samples, androgen-stimulated benign prostate (AS-BP), androgen-stimulated primary prostate cancer (AS-CaP), and recurrent primary tumors (RCaP) were obtained as previously described [Mohler J L, et al. Clinical cancer research: an official journal of the American Association for Cancer Research. 2004; 10:440-448]. The epithelial immortalized non-transformed cell line HPr-1 and the derived AR positive HPr-1AR are as described [Ling M T, et al. J Endocrinol. 2001; 170:287-296].

Mice and dietary intervention—All the mouse work was carried out at the Department of Laboratory Animal Research at RPCI, using known approaches. Briefly, male TRAMP (Transgenic Adenoma of Mouse Prostate) mice, heterozygous for the Pb-Tag transgene, ([C57BL/6J X FVB] F1 background), were bred in the RPCI Institute animal housing facility in accordance with an Institutional Animal Care and Use Committee-approved protocol. Mice were weaned at 3 weeks of age. At the time of weaning the mice were randomly assigned to two cohorts of at least 25 mice characterized by different folate concentrations in their diet using established techniques.

HPLC analyses—HPLC analyses were carried out using standard techniques. Standards for SAM and SAH were purchased from Sigma. All analyses were carried out on a reverse-phase Econosil (C18) column (5 µm particle size, 4.6×250 mm) (Fisher Scientific) with a C18 guard column assembled on the Waters 2796 Bioseparation module of the Biopolymer Facility, at RPCI (Buffalo, N.Y.).

Prostate TMA—The RPCI_PrCa7 tissue micro array (TMA) was prepared and analyzed at the RPCI Pathology core facility. Three 1-millimeter (mm) tissue cores from over 75 formalin-fixed paraffin embedded donor blocks of prostatic adenocarcinoma were precisely arrayed into a new recipient paraffin block. Specimens for controls consisted of multiple cores of normal tissue from 10 different organs including heart, colon, kidney, adrenal, ovary, myometrium, brain, thyroid, lung, and prostate. One slice was stained by immunohistochemistry (IHC) with p63 and the high molecular weight racemase, which are overexpressed in cancer tissues, to distinguish normal, prostatic intraepithelial neoplasia, and prostatic adenocarcinoma. Other IHC were carried out on other slices, including MTAP (Protein Tech group inc, cat #11475-1-AP), using known approaches.

Fluorescence in situ hybridization (FISH): FISH was carried out on the same TMA with PCR-validated probes from the RPCI BAC library collection hybridizing to either p16 (RP11-14912) or MTAP (RP11-70L8). A commercially available spectrum green CEPS probe (Vysis, Downers Grove, Ill.) was co-hybridized with the probe of interest (spectrum orange) for evaluation of copy number gain or loss. Cutoff values for the determination of each FISH were established by manually scoring 200 nuclei from forty 0.6-millimeter cores representing normal tissue from 10 different organs. Cutoff values were then established by calculation of the mean plus three times the standard deviation of the number of normal cells with a false-positive signal. For all FISH done in this study a total of at least 200 nuclei were manually scored for every case.

RNA interference of MTAP—293T cells were transfected in a 6 well plate with MTAP shRNA constructs (A, B, C, and D) from a pGIPZ lentiviral shRNA library or pGIPZ scrambled shRNA non-silencing control, and packaging plasmids psPAX2 (contains GAG/POL/REV/TAT) and pMD2.G (contains ENV). Lentiviral containing supernatant from 293T cells was removed at 48 and 72 hours, filtered through 0.45 uM PES filter, and used to infect LNCaP cells. Silencing was assessed and sequences B and D were deemed best. Populations B and D were then sub-cloned to obtain pure clonal populations.

Western Blotting—Whole cell extracts were prepared in RIPA buffer (150 mM NaCl, 1.0% NP-40, 0.5% deoxycholate, 0.1% SDS, 50 mM Tris-HCl pH 8.0, 5 mM EDTA and 0.5 mM PMSF) supplemented with 1× proteinase inhibitor. Protein concentrations were determined by Bradford Assay (Thermo Scientific, Cat #1856209). Samples were resolved on polyacrylamide gels and transferred onto PVDF membranes (Biorad, Cat #162-0177). Blots were incubated with primary antibodies overnight at 4° and with secondaries for 1.5 hours at room temperature. Signals were visualized using Pierce ECL western blotting substrate (Thermo Scientific, Cat #32209) and exposed to film. MTAP for Westerns was purchased from Proteintech™ (Cat #11475-1-AP. SRM and SMS were purchased from Abcam® (Cat #ab111884 and ab156879). B-actin antibody for Westerns was purchased from Sigma-Aldrich (Cat #A5441) and GAPDH was from Santa Cruz Biotecnology Inc. (Cat #sc-25778). Films were scanned using the Biorad ChemiDoc XRS, and band intensities were calculated using Image Lab™. Intensity values were normalized to B-actin loading control band intensities and made relative to control treatment conditions.

Clonogenicity assays—3,000 LNCaP cells either silenced for MTAP or transfected with the control vector, were seeded in a 6 well plate in duplicate in methionine-free and folate-free RPMI medium supplemented with 10% dialyzed serum, 10-9 R1881, 24 µM methionine (the minimal amount required by prostate cells to grow in vitro), 2 µg/ml puromycin, and folate as indicated (100 nM as a slight deficiency or 200 nM as control). Cells were grown till visible colonies formed (about three weeks). Cells were fixed in 1% methanol, stained with 1% Giemsa, and the colonies were counted.

Human cell line xenografts with RNA interference—Male Athymic Nude mice were castrated and pelleted with testosterone to bring their serum levels up to that of an adult human male and then randomly assigned to two groups. 1×106 clonally derived LNCaP cells transfected with either shScrambled control or shMTAP-D were subcutaneously injected onto the flank of each mouse. Within each group of scramble control and shMTAP, there were two cohorts of 10 mice each. Mice were fed either folic acid control or supplemented diets (diet detail above) for a total of 4 cohorts, 10 mice per cohort. The experiment was repeated once to give a total of 20 mice per cohort. Tumor measurements were assessed and recorded twice a week.

Figure 6:
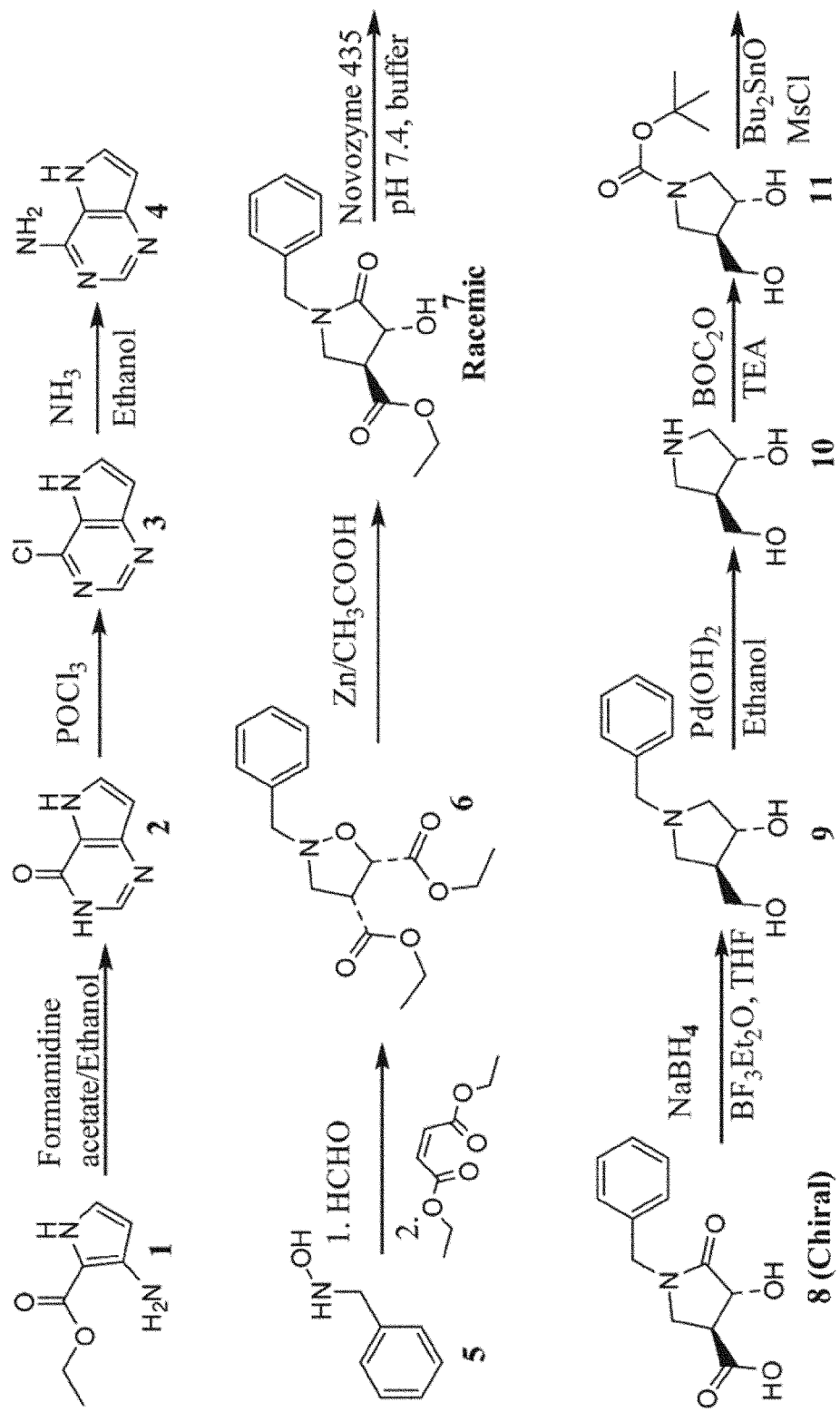
FIG. 6. Scheme I: Synthesis of (3R,4S)-1-[(9-Deaza-adenin-9-yl)methyl]-3-hydroxy-4-(methylthiomethyl)-pyrrolidine.
Figure 6:
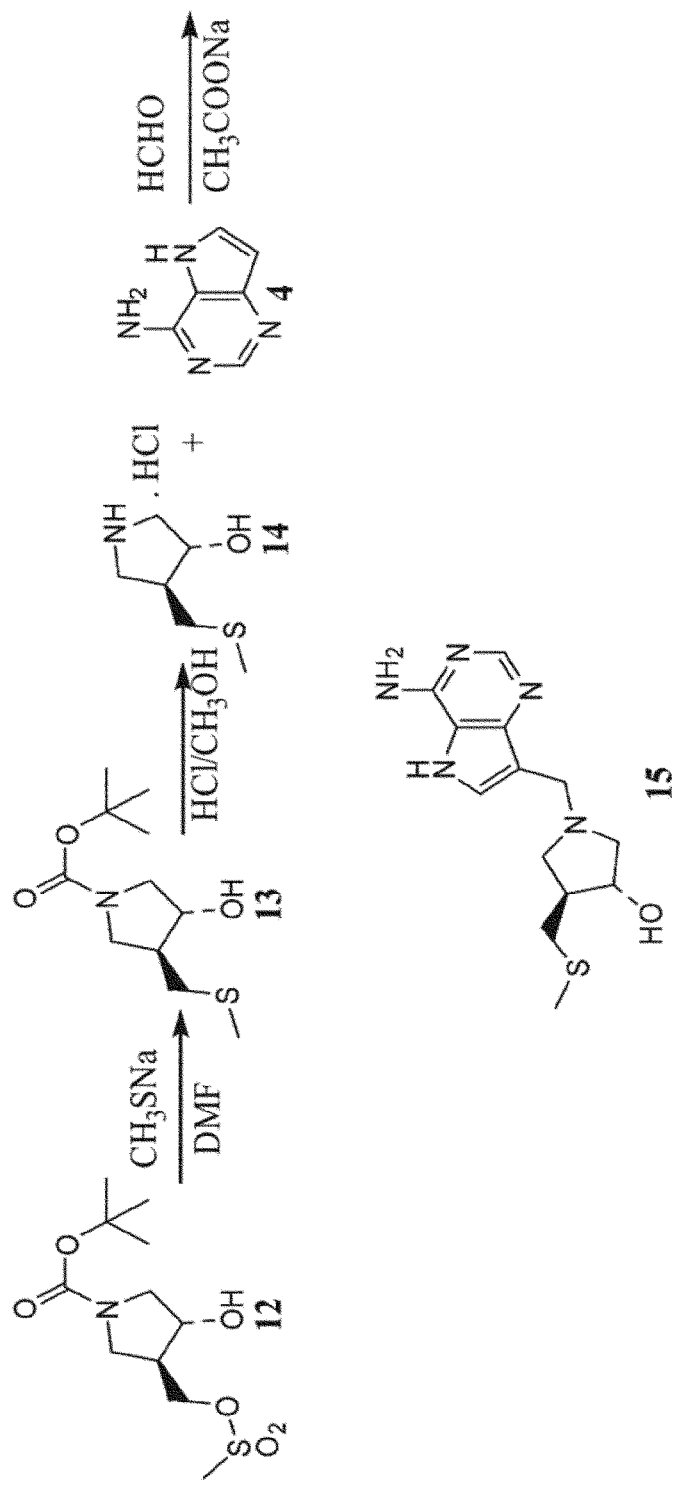

IC50—The MTAP inhibitor (3R,4S)-1-[(9-Deaza-adenin-9-yl)methyl]-3-hydroxy-4-(methylthiomethyl)-pyrrolidine, or MT-DADMe-Immucillin-A (MTDIA) was synthesized following the synthesis scheme shown in FIG. 6 and based on a known approach. Cells were seeded at 125,000 cells/well (PC-3, DU145, LNCaP) in triplicate in 2 mLs of RPMI medium supplemented with 10% fetal bovine serum, and 1% penicillin streptomycin. After 24 hours the MTDIA and/or MTA was added at the indicated concentrations. Both medium and drug were refreshed every 48 hours. Every 96 hours the cells were trypsinized, ~2% of cells were removed and counted by trypan blue exclusion and the rest were replated into a larger vessel.

Human cell line xenografts with pharmacological treatment—1×106 wild type LNCaP cells were subcutaneously injected onto the flank of pelleted nude mice. At time of injection animals were randomly assigned to one of the following three groups; control, 9 or 21 mg/kg MTDIA in the drinking water with 20 mice in each group. Tumor measurements were assessed and recorded twice a week. Animals were sacrificed once tumors reached 2 cm3 or at the end point of the experiment (91 days).

EXAMPLE 6

As demonstrated in the foregoing Examples, in CaP cell lines we found 8 days of treatment significantly blocked cell proliferation with an IC50 of 85 nM, and shRNA knockdown of MTAP completely blocked LNCaP xenograft growth in nude mice. Moreover, MTDIA dramatically blocked LNCaP xenograft growth in nude mice given 21 mg/kg in the drinking water at the time of implantation.

Figure 10:
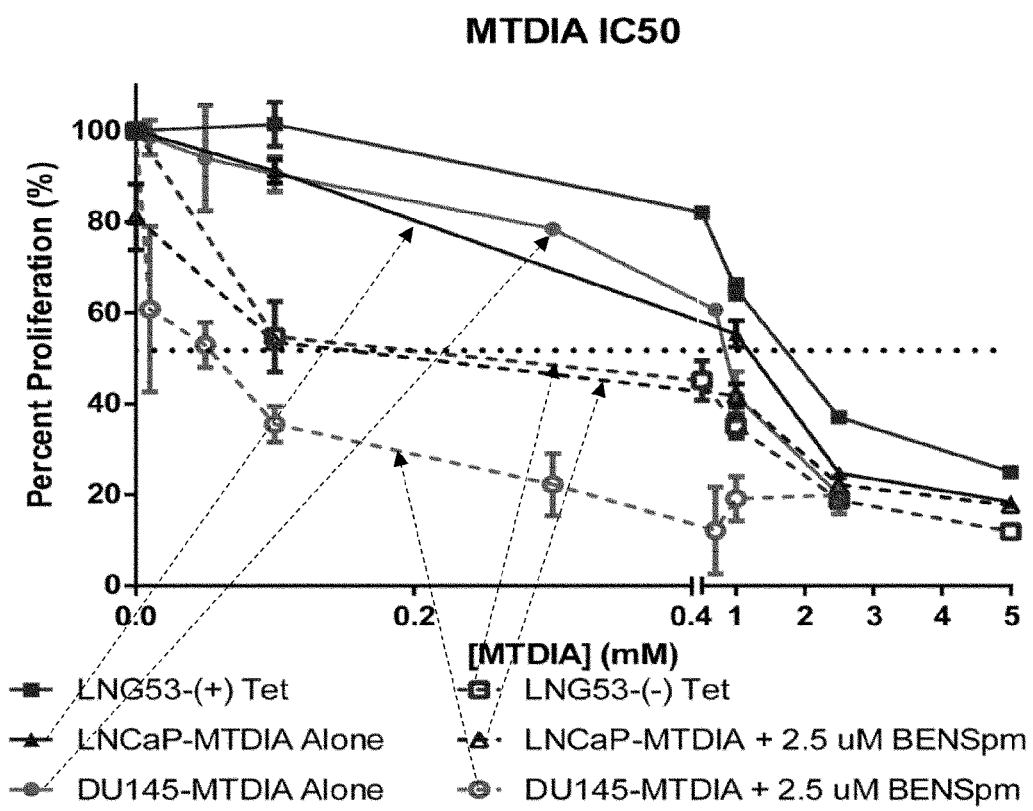
FIG. 10 shows antiproliferative activity of MTDIA: LNCaP cells overexpressing Spermidine/Spermine N1-Acetyltransferase 1 (SAT1) in Tet-off system are more sensitive to MTDIA when SAT1 is overexpressed. Tet was removed 24 hours prior to 96 hr treatment with MTDIA. Wild type LNCaP and DU145 cells become more sensitive to MTDIA in the presence of 2.5 µM BENSpm. Cells were pre-treated with BENSpm for 24 hours followed by 96 hr treatment with MTDIA.
Figure 11:
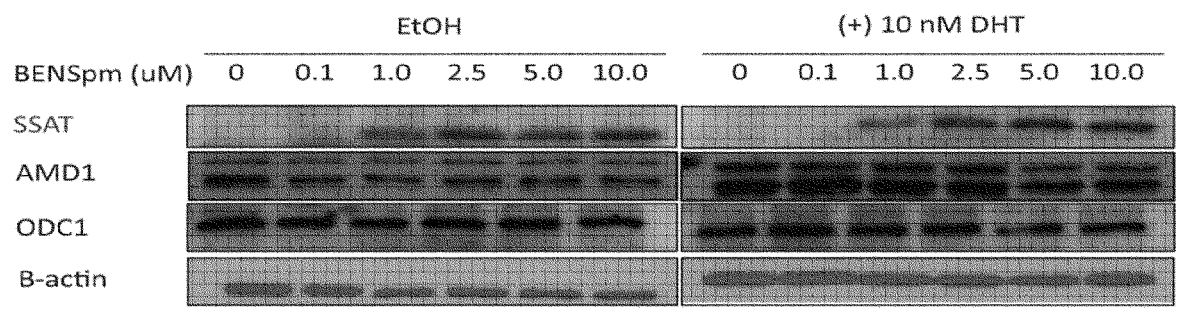
FIG. 11 depicts a Western blot showing AMD1, ODC1, SAT1 and B-actin protein expression in wild type LNCaP cells pretreated with +/−DHT for 24 hours followed by BENSpm for 96 hours.

We next analyzed whether the metabolic stress in CaP cells caused by high biosynthetic flux to maintain polyamine pools can be enhanced by increasing the activity of SAT1. We tested whether this could cause increased secretion of acetylated polyamines, putting intracellular pools in deficit, which should necessitate more biosynthesis, and should therefore potentiate any benefit of inhibiting the MSP. To conduct this analysis we used LNCaP cells that stably overexpress SAT1 in a Tet-off system (LNG53 cells, described in Kee, K., et al. J Biol Chem 279, 27050-27058 (2004)). These cells were shown to maintain intracellular polyamine levels despite secreting significant amounts of acetylated polyamines into the media. Consequently, these cells exhibited a significant decrease in their SAM pools due to the consumption of SAM for polyamine biosynthesis (Kee, et al., 2014). Using these same cells, we demonstrated that high level SAT1 activity ((−) Tet conditions, (FIG. 10) made the cells much more sensitive to MSP inhibition with MTDIA. These cells were shown to maintain intracellular polyamine levels despite secreting significant amounts of acetylated polyamines into the media. We then determined that the treatment of LNCaP cells with BENSpm in a range of doses from 0.1 to 10 µM resulted in increased SAT1 mRNA (data not shown) and protein (FIG. 11). Furthermore, SAT1 activity, exhibited a dose dependent increase in response to BENSpm treatment from ~17-40 fold in (+) dihydrotestosterone (DHT) conditions and ~6-20 fold in (−) DHT conditions (data not shown). Meanwhile, there were minimal effects on the polyamine biosynthetic enzymes, ODC1, and s-adenosylmethionine decarboxylase (AMD1), (FIG. 11). As shown in FIG. 10, BENSpm treatment was nearly as effective as exogenous overexpression of SAT1 in terms of increasing sensitivity to MTDIA (indicated with arrows). Notably, BENSpm also strongly increased sensitivity to MTDIA in the AR negative DU145 cell line (indicated with arrows). When LNCaP cells were treated with 2.5 µM BENSpm alone there was no effect on proliferation (not shown). Yet this dose of BENSpm greatly increased sensitivity to MTDIA (FIG. 10).

Figure 12:
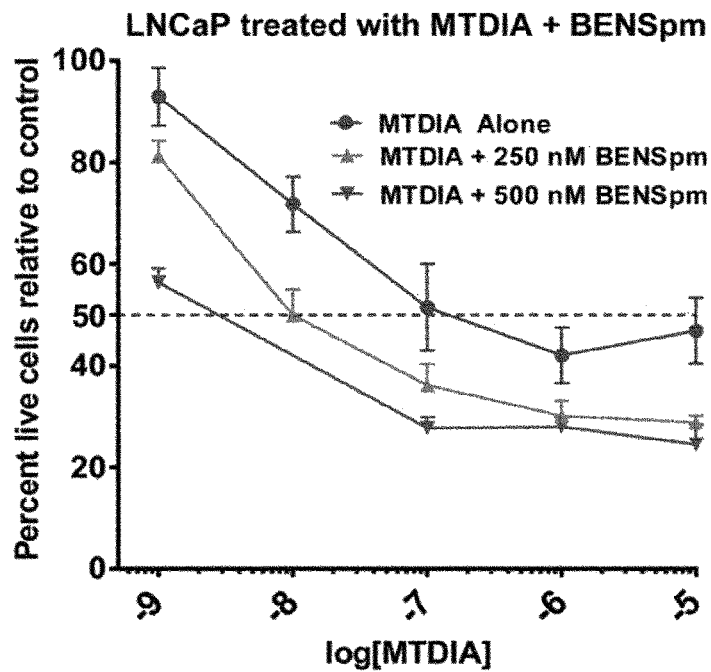
FIG. 12 shows synergistic antiproliferative activity of MTDIA and BENSpm. Proliferation curves of the androgen sensitive cell line (LNCaP) treated for 8 days in the presence of 20 uM MTA with vehicle control, 1 nM, 10 nM, 100 nM, 1 uM or 10 uM MTDIA in the presence or absence of 250 or 500 nM BENSpm.
Figure 13:
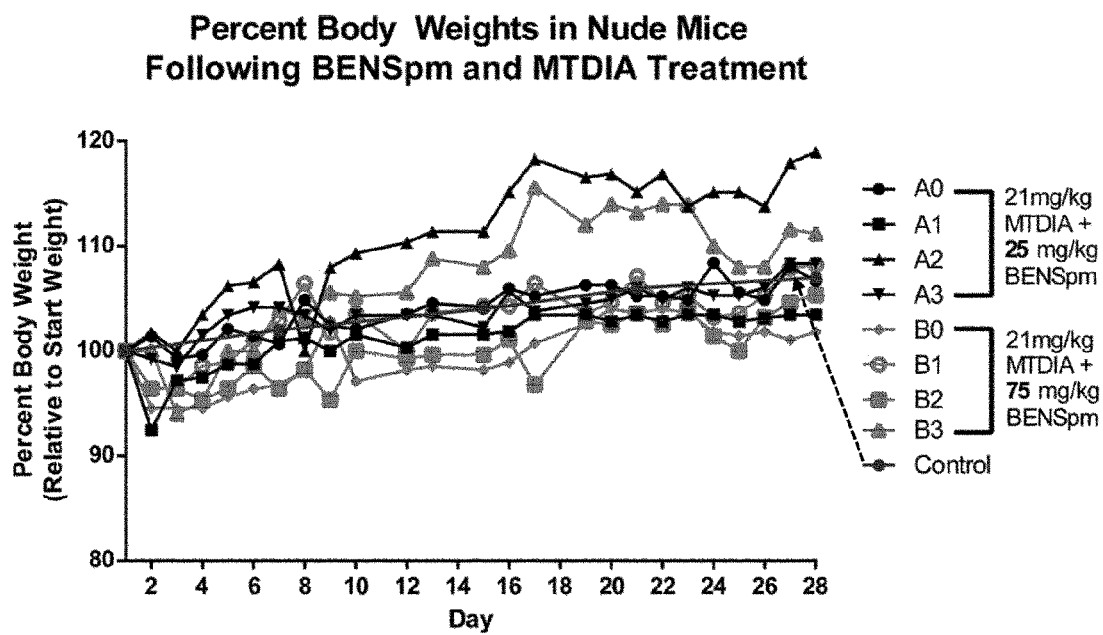
FIG. 13 demonstrates results from a toxicity study using the effective dose of MTDIA (21 mg/kg) plus either 75 or 25 mg/kg BENSpm in comparison to a control group. There were 4 animals per group and the study lasted 28 days. There were no signs of toxicity including blood chemistry, CBC, coagulation, and organ weights. These results demonstrate that the drug combination is not prohibitively toxic.

We then treated cells with a combination of BENSpm and MTDIA at varying concentrations. Results are shown in the proliferation curves in FIG. 12 obtain using the androgen sensitive cell line LNCaP treated for 8 days in the presence of 20 uM MTA with vehicle control, 1 nM, 10 nM, 100 nM, 1 uM or 10 uM MTDIA in the presence or absence of 250 or 500 nM BENSpm. Combination Indexes (CI) were calculated to mathematically determine synergy using the Chou-Talalay method with the CompuSyn software. Almost all combinations gave CIs well below 1, indicative of a synergistic relationship between MTDIA and BENSpm in LNCaP cells (summarized in Table 2). These data demonstrate that pharmacological enhancement of SAT1 activity is achievable in CaP cells, has demonstrable effects on key metabolites, and makes cells more sensitive to MSP inhibition. Furthermore, we analyzed the mechanism of action of these drugs in vitro. RNAseq results indicate that these drugs affect their target pathways, but also a number of connected pathways. The most highly affected pathways following treatment are pathways involved in the consumption and production of acetyl-CoA, which is consumed to acetylate polyamines. Therefore it is possible these drugs could act through altered fatty acid synthesis, a key pathway involved in CaP progression. Further, by RNAseq and Western blot we found that fatty acid synthase is downregulated upon treatment with MTDIA and BENSpm. Thus, the presently provided metabolic based approach comprises an alternative therapeutic strategy for eligible patients requiring treatment or for higher risk patients ineligible for prostatectomy because of comorbidities. Additionally, FIG. 13 demonstrates results from a toxicity study using the effective dose of MTDIA (21 mg/kg) plus either 75 or 25 mg/kg BENSpm in comparison to a control group. There were 4 animals per group and the study lasted 28 days. There were no signs of toxicity including blood chemistry, CBC, coagulation, and organ weights. Thus, these results demonstrate that the drug combination is not prohibitively toxic.

TABLE 2

| CI Index | | BENSpm | | | |
|---|---|---|---|---|---|
| | | 100 nM | 250 nM | 500 nM | 1000 nM |
| MTDIA | 1 nM | 20.5 | 0.42 | 0.19 | 0.4 |
| | 10 nM | 0.1 | 0.09 | 0.13 | 0.43 |
| | 100 nM | 0.04 | 0.07 | N/A | 0.3 |
| | 1 uM | 0.04 | 0.07 | 0.13 | 0.29 |
| | 10 uM | 0.07 | 0.12 | 0.14 | 0.3. |

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method that synergistically inhibits growth of prostate cancer (CaP) in an individual, the method comprising administering to the individual i) methylthio-DADMe-Immucillin (MTDIA) as an inhibitor of methionine salvage pathway in prostate of the individual;

and ii) a polyamine analogue selected from the group consisting of N(1),N(11)-bisethylnorspermine (BENSpm), alpha-difluoromethylornithine (DFMO), PG-11047, $N^1$-ethyl-$N^{11}$-[(cyclopropyl)methyl]-4,8,-diazaundecane (CPENSpm), aspirin, and combinations thereof.

2. The method of claim 1, wherein the individual has been diagnosed with, or is suspected of having androgen sensitive prostate cancer (AS-CaP) or Castration recurrent CaP (CR-CaP).

3. The method of claim 1, wherein the polyamine analogue comprises the BENSpm.

4. The method of claim 2, wherein the methionine salvage pathway inhibitor is MTDIA and the polyamine analogue is BENSpm.

5. A method comprising contacting prostate tissue of an individual in need thereof with a combination of i) methyl-thio-DADMe-Immucillin (MTDIA) as an inhibitor of methionine salvage pathway in prostate of the individual; and ii) a polyamine analogue selected from the group consisting of N(1),N(11)-bisethylnorspermine (BENSpm), alpha-difluoromethylornithine (DFMO), PG-11047, $N^1$-ethyl-$N^{11}$-[(cyclopropyl)methyl]-4,8,-diazaundecane (CPENSpm), aspirin, and combinations thereof, wherein contacting the prostate tissue with a combination of MTDIA and the polyamine analogue results in the synergistic inhibition of the growth of tissue in the prostate of the individual.

6. The method of claim 5, wherein the individual is diagnosed with or is suspected of having prostate cancer (CaP) or benign prostate hyperplasia (BPH).

7. The method of claim 5, wherein the polyamine analogue comprises the BENSpm.

8. The method claim 6, wherein the methionine salvage pathway inhibitor is the MTDIA and the polyamine analogue is the BENSpm.

9. The method of claim 8, wherein the individual has been diagnosed with, or is suspected of having BPH.

10. The method of claim 8, wherein subsequent to the contacting the prostate tissue growth of prostate tissue is synergistically inhibited.

11. The method of claim 9, wherein subsequent to the contacting the prostate tissue the size of the prostate gland in the individual is reduced.

* * * * *